(12) United States Patent
Satyanarayana Reddy et al.

(10) Patent No.: US 8,168,828 B2
(45) Date of Patent: May 1, 2012

(54) PROCESS FOR THE PREPARATION OF PREGABALIN

(75) Inventors: Manne Satyanarayana Reddy, Hyderabad (IN); Srinivasan Thirumalai Rajan, Hyderabad (IN); Sajja Eswaraiah, Hyderabad (IN); Revu Satyanarayana, East Godavari (IN)

(73) Assignee: MSN Laboratories, Limited, Andhra Pradesh Hyderabad (IN)

( * ) Notice: Subject to any disclaimer, the term of this patent is extended or adjusted under 35 U.S.C. 154(b) by 0 days.

(21) Appl. No.: 12/666,133

(22) PCT Filed: Mar. 24, 2008

(86) PCT No.: PCT/IN2008/000174
§ 371 (c)(1),
(2), (4) Date: Dec. 22, 2009

(87) PCT Pub. No.: WO2009/001372
PCT Pub. Date: Dec. 31, 2008

(65) Prior Publication Data
US 2010/0179345 A1   Jul. 15, 2010

(30) Foreign Application Priority Data

Jun. 25, 2007 (IN) .......................... 1344/CHE/2007
Jan. 14, 2008 (IN) .......................... 114/CHE/2008

(51) Int. Cl.
C07C 237/06 (2006.01)
C07C 227/30 (2006.01)
C07C 229/12 (2006.01)
(52) U.S. Cl. ....................................... 564/197; 562/553
(58) Field of Classification Search .................. 564/197
See application file for complete search history.

(56) References Cited

U.S. PATENT DOCUMENTS

| 5,599,973 | A | 2/1997 | Silverman et al. |
| 5,637,767 | A | 6/1997 | Grote et al. |
| 2003/0212290 | A1 | 11/2003 | Burk et al. |
| 2007/0197827 | A1* | 8/2007 | Kansal et al. ..................... 564/1 |

FOREIGN PATENT DOCUMENTS

| CZ | 297970 B6 | 5/2007 |
| EP | 0254685 A2 | 1/1988 |

OTHER PUBLICATIONS

CAS Registry No. 766508-49-0, entered STN on Oct. 21, 2004.*
Hong-Ju et al. Bioorg. Med. Chem. Lett. 2004, 14, 2537-2541.*
English Translation of CZ 297970, translated Mar. 2011.*
International Search Report, PCT/IN2008/000174, 4 pp., Date of Mailing: Oct. 11, 2010.
PCT International Preliminary Report on Patentability, PCT/IN2008/000174, 1 pg., Date of Issuance of Report: Oct. 19, 2010.
PCT Written Opinion of the International Searching Authority, PCT/IN2008/000174, 3 pp., Date of Mailing: Oct. 11, 2010.
Armstrong, A., et al., "Diastereoselective Conjugate Addition of Cyanide to α,β-Unsaturated Oxazolidinones: Enantioselective Synthesis of ent-Pregabalin and Baclofen," SYNLETT, No. 10, pp. 1589-1591 (Received Mar. 9, 2006).
"Pregabalin," Drugs of the Future, 24(8): 8620870, (1999) (no month).
Mita, T., et al., "Catalytic Enantioselective Conjugate Addition of Cyanide to α,β-Unsaturated N-Acylpyrroles," J. AM. Chem. Soc., 127, 514-515 (2005) (no month).
Concellón, J. M. and Concellón, C., "Aldol-type Reactions of Unmasked Iodoacetic Acid with Carbonyl Compounds Promoted by Samarium Diiodide: Efficient Synthesis of Carboxylic 3-Hydroxyacids and Their Derivatives," J. Org. Chem., 71, No. 12, 4428-4432 (2006) (no month).
Andruszkiewicz, R., and Silverman, R.B., "A Convenient Synthesis of 3-Alkyl-4-Aminobutanoic Acids," Communications, pp. 953-955(1989).
Sammis, G.M. and Jacobsen, E.N., "Highly Enantioselective, Catalytic Conjugate Addition of Cyanide to α,β-Unsaturated Imides," J. Am. Chem. Soc., 125:4442-4443 (2003).
Yamamoto, K., et al., "Stereoselective Synthesis of (E)-Alkylideneseuccinates by Palladium-catalyzed Carbonylation," The Chemical Society of Japan, 58:3397-3398(1985).

* cited by examiner

Primary Examiner — Joseph Kosack
Assistant Examiner — Matthew Coughlin
(74) Attorney, Agent, or Firm — Hamilton, Brook, Smith & Reynolds, P.C.

(57) ABSTRACT

The present invention encompasses novel intermediates of pregabalin, namely 3-cyano-5-methyl hexanamide (28) and 3-(amino methyl)-5 methyl hexanamide (29), and processes for their preparation. The invention also encompasses a process for converting the novel pregabalin intermediates into pregabalin, Formula (I): The present invention further provides a cost effective method for the synthesis of (S)-pregabalin, which involves the recovery of mandelic acid and tartaric acid used in the resolution process and recycling them, increasing the yields of the final product formed, which substantially reduced the cost of the production.

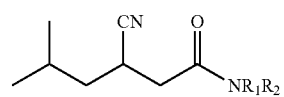

28

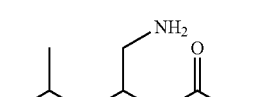

29

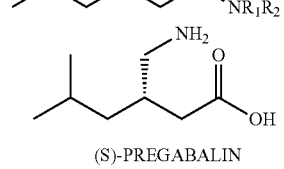

(S)-PREGABALIN

19 Claims, 1 Drawing Sheet

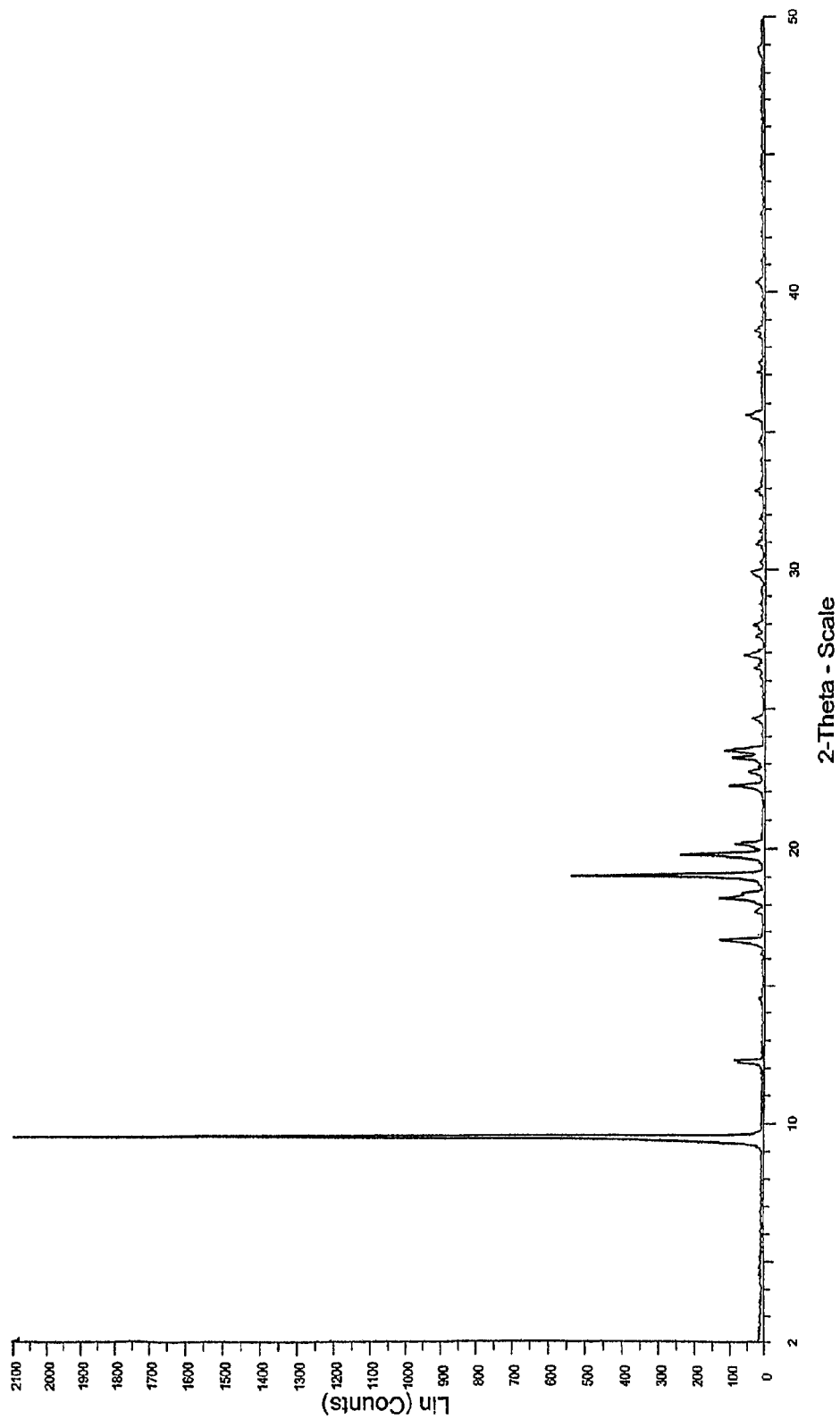

PROCESS FOR THE PREPARATION OF PREGABALIN

RELATED APPLICATIONS

This application is the U.S. National Stage of International Application No. PCT/IN2008/000174, filed Mar. 24, 2008, which designates the U.S., published in English, and claims priority under 35 U.S.C. §§119 or 365(c) to Indian provisional application no. 1344/CHE/2007, filed Jun. 25, 2007 and Indian patent application No.: 114/CHE/2008, filed on Jan. 14, 2008. The entire teachings of the above applications are incorporated herein by reference.

FIELD OF THE INVENTION

The present invention encompasses novel intermediates of pregabalin, namely 3-cyano-5-methyl hexanamide of general formula-28 and 3-(aminomethyl)-5 methyl hexanamide of general formula-29, and processes for their synthesis. The invention also encompasses a process for converting the novel pregabalin intermediates into pregabalin.

It also encompasses a cost effective and economically useful method for the preparation of (S)-pregabalin. (S)-Pregabalin is chemically known as (S)-(+)-3-(amino methyl)-5-methylhexanoic acid represented as a compound of formula-1.

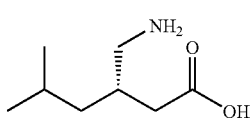

Formula-1

Pregabalin is also known as γ-amino butyric acid or (S)-3-isobutyl GABA. (S)-pregabalin has been found to activate GAD (L-glutamic acid decarboxylase). (S)-pregabalin has a dose dependent protective effect on-seizure, and is a CNS-active compound. (S)-pregabalin is useful in anticonvulsant therapy, due to its activation of GAD, promoting the production of GABA, one Of the brain's major inhibitory neurotransmitters, which is released at 30 percent of the brains synapses. (S)-pregabalin has analgesic, anticonvulsant, and anxiolytic activity. (S)-pregabalin is marketed under the trade name LYRICA®.

BACKGROUND OF THE INVENTION

Several processes were reported for the synthesis of (S)-Pregabalin. One such process is illustrated in drugs of the future, 24 (8), 862-870 (1999), represented as scheme-1. In which 3-isobutylglutaric acid, compound 2, is converted into the corresponding anhydride, compound 3, by treatment with refluxing acetic anhydride. The reaction of the anhydride with $NH_4OH$ produces the glutaric acid mono-amide, compound 4, which is resolved with (R)-1-phenylethylamine, yielding the (R)-phenyl ethylamine salt of (R)-3-(carbamoylmethyl)-5-methylhexanoic acid, compound 5. Combining the salt with an acid liberates the (R)-enantiomer, compound 6. Finally, a Hoffmann's degradation with $Br_2/NaOH$ provides (S)-Pregabalin. A disadvantage of this method is that, it requires separating the two enantiomer thereby resulting in the loss of half of the product, such that the process cost is high.

Scheme-1:

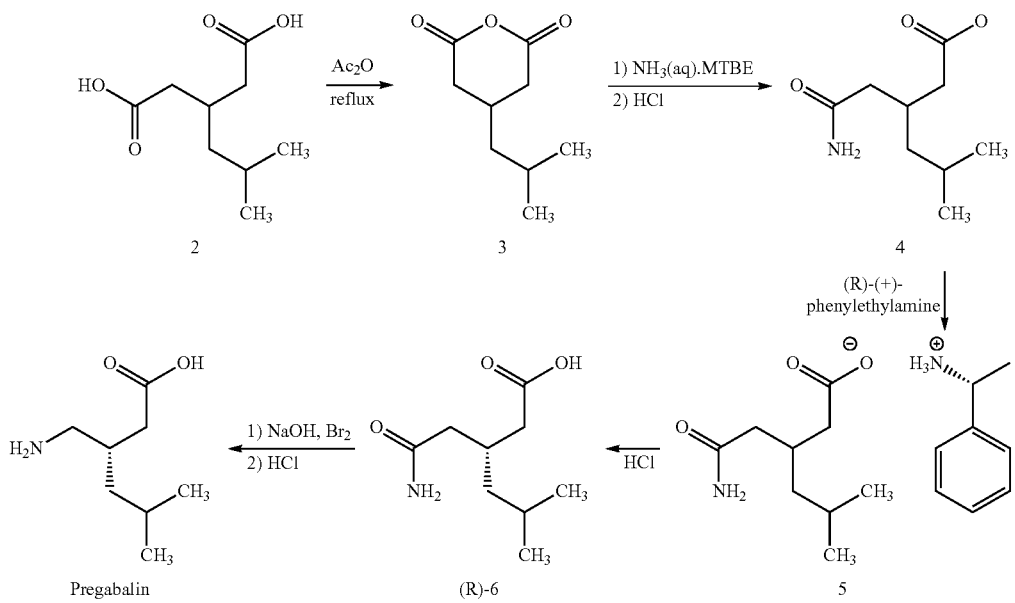

A few stereo selective processes for the synthesis of (S)-Pregabalin have been disclosed. For example, U.S. Pat. No. 5,599,973 discloses the preparation of (S)-Pregabalin using stoichiometric (+)-4-methyl-5-phenyl-2-oxazolidinone as a chiral auxiliary that may be recycled. In general, however, that route is of limited use for scale-up, principally due to the low temperature required for the reactions, the use of pyrophoric reagent such as butyl lithium, and due to side reactions, which resulted in a low overall yield.

Another process is disclosed in U.S. Patent Application Publication No. 2003/0212290, which discloses asymmetric hydrogenation of a cyano-substituted olefin, compound 7, to produce a cyano precursor of (S)-3-(amino methyl)-5-methyl hexanoic acid, compound 8, as seen in scheme 2.

Scheme-2:

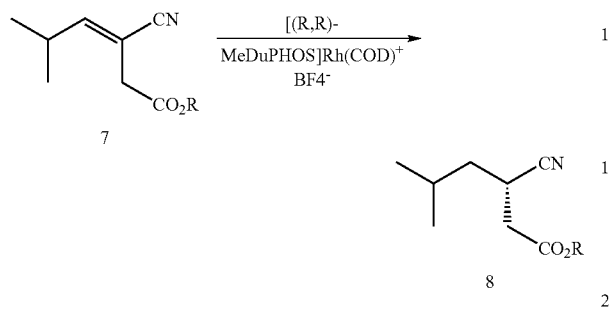

Subsequent reduction of the nitrile with compound 8 by catalytic hydrogenation produces (S)-Pregabalin. The cyano hexenoate starting material, compound 7, is prepared from 2-methyl propanal and acrylonitrile (Yamamoto et al, *Bull. Chem. Soc. Jap.*, 58, 3397 (1985)). However, the disclosed method requires carbon monoxide under high pressure, raising serious problems in adapting this scheme for production scale processes.

A process published by G. M. Sammis, et al., *J. Am. Chem. Soc.*, 125(15), 4442-43 (2003), takes advantage of the asymmetric catalysis of cyanide conjugate addition reactions. The method discloses the application of aluminium salen catalysts to the conjugate addition of hydrogen cyanide to α,β-unsaturated imides as shown in scheme-3. Reportedly, TMSCN is a useful source of cyanide that can be used in the place of HCN. Although the reaction is highly selective, this process is not practicable for large scale production due to the use of highly poisonous reagents. Moreover, the last reductive step requires high pressure hydrogen, which only adds to the difficulties required for adapting this scheme for a production scale process.

Scheme-3:

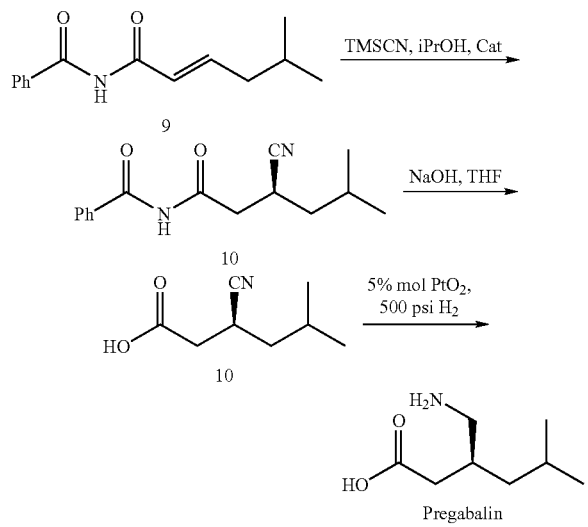

In 1989, Silverman reported a convenient synthesis of 3-alkyl-4-amino acids compounds in 'Synthesis', Vol. 12, 953-954 (1989). Using 2-alkenoic esters as a substrate, a series of GABA analogs were produced by Michael addition of nitro methane to α,β-unsaturated compounds, followed by hydrogenation at atmospheric pressure of the nitro compound to amine moiety as depicted in scheme 4.

Scheme-4:

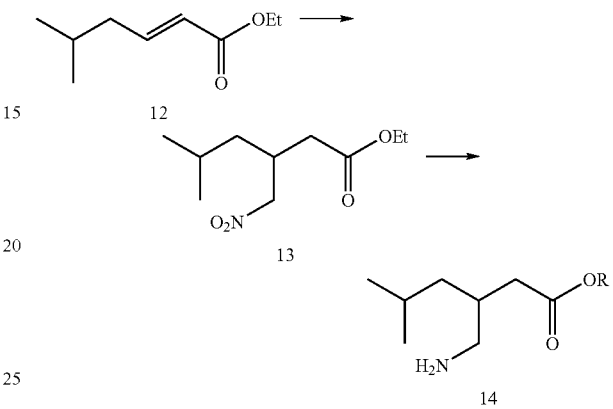

Further resolution of compound 14 may be employed to resolve Pregabalin. This, of course, results in the loss of 50 percent of the product, a serious disadvantage. However, the disclosed methodology reveals that the nitro compound can serve as an intermediate for the synthesis of 3-alkyl-4-amino acids.

Due to the activity of GABA as an inhibitory neurotransmitter, and its effect on convulsive states and other motor dysfunction, development of a drug which can stimulate the release of GABA has become important. Pregabalin a GAD activator has the ability to stimulate the release of GABA and to suppress seizures while avoiding the undesirable side effect of ataxia. It has been discovered that anticonvulsant effect of isobutyl-GABA is stereoselective. That is, S-isomer of Pregabalin shows better anticonvulsant activity than the R-stereoisomer. Thus, it would be beneficial to have an efficient process for the synthesis of the (S)-isomer of pregabalin.

The consumption of pregabalin has increased in high volumes and all the reported processes provide very poor yields of (S)-pregabalin. Hence there is a need to develop a method of preparation of pregabalin, which provides high yields, is cost effective and commercially viable, and which can be adapted to an industrial scale.

BRIEF DESCRIPTION OF THE INVENTION

The present invention relates to a process for the preparation of novel intermediate compounds namely 3-cyano-5-methyl hexanamide, hereafter designated as compound of general formula-28 and 3-(amino methyl)-5 methyl hexanamide, hereafter designated as compound of general formula-29, which are the key intermediates in the novel route for the synthesis of pregabalin.

The first aspect of the present invention deals with a process for the preparation of novel intermediate of general formula-28, which is useful for the synthesis of pregabalin. The process comprises of;

a) condensation of aldehyde compound of formula-15,

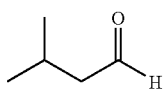
Formula-15 with an α-halo ester compound of formula-16,

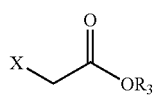
Formula-16 in the presence of zinc metal and a suitable catalyst, in a suitable polar solvent provides β-hydroxy ester compound of formula-17,

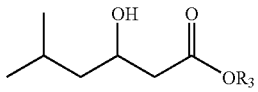
Formula-17 b) hydrolysis of the β-hydroxy ester compound of formula-17, with an alkali or alkaline metal base, in a protic solvent provides a β-hydroxy acid compound of formula-18,

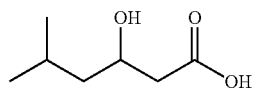
Formula-18 c) reacting the β-hydroxy acid compound of formula-18, with an halogenating agent in an aprotic solvent, followed by subsequent reaction with a secondary amine $NHR_1R_2$ of formula-19, provides a β-halo amide compound of formula-20,

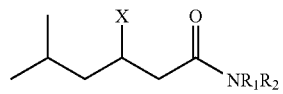
Fomula-20 d) treating the β-halo amide compound of formula-20, with an cyanide source in an polar aprotic solvent, provides the novel intermediate the β-cyano amide, compound of formula-28,

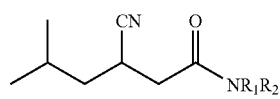
Formula-28

An alternate process for the preparation of novel intermediate of general formula-28, comprises of the following steps, a) Hydrolyzing the diester compound of formula-21,

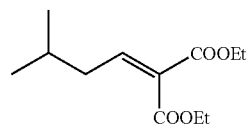
Formula-21 in presence of a suitable alkali metal or alkaline earth metal base in a suitable solvent gives the carboxylic acid compound of formula-22,

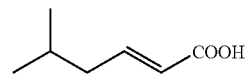
Formula-22 b) reacting the carboxylic acid compound of formula-22 with a suitable amine ($NHR_1R_2$), in presence of a suitable organic solvent gives an amino amide compound of general formula-23,

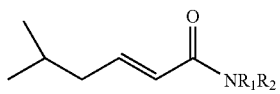
Formula-23 c) reacting the amide compound of general formula-23 with a suitable cyanide source in presence of a phase transfer catalyst in a suitable solvent gives cyanide compound of general formula-28,

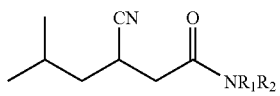
Formula-28

The second aspect of the present invention relates to the preparation of novel intermediate of general formula-29, useful in the synthesis of pregabalin. The process for the synthesis of the novel intermediate comprises of;

a) Reaction of 3-isobutylglutaric acid anhydride compound of formula-3,

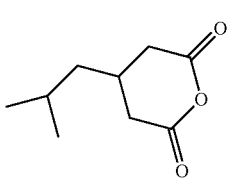
Formula-3 b) with a secondary amine $NHR_1R_2$ of general formula-19, in a suitable solvent, provides a compound of general formula-26,

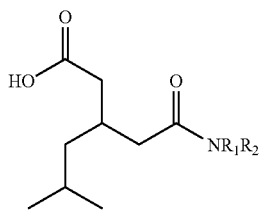

Formula-26 c) reaction of compound of general formula-26, with thionyl chloride followed by ammonia provides the diamide compound of general formula-27,

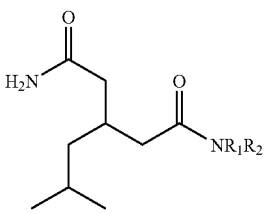

Formula-27 d) subjecting the compound of formula-27 to Hoffman's degradation provides the compound of general formula-29,

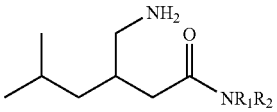

Formula-29

The third aspect of the present invention encompasses the novel process for the preparation of (S)-pregabalin involving the novel intermediates, 3-cyano-5-methyl hexanamide compounds of general formula-28 and 3-(amino methyl)-5-methyl hexanamide, compounds of general formula-29.

The fourth aspect of the present invention relates to an improved cost effective and economically useful method for the preparation of (S)-pregabalin.

Advantages of the Present Invention:
Provides a novel process for the preparation of (S)-pregabalin with high yields and high purity.
Provides novel intermediate compounds of formulae 23, 28, 29, 30 and 31.
Provides a novel process for the preparation of intermediate compound of formula-29.
Eco-friendly and cost effective process.

BRIEF DESCRIPTION OF THE DRAWINGS

FIG. 1: Illustrates the powder X-ray diffraction pattern of crystalline Pregabalin.

DETAILED DESCRIPTION OF THE INVENTION

Unless otherwise indicated, this disclosure uses definitions provided below. As used herein, the term "alkyl" refers to straight chain or branched hydrocarbon groups, generally having specified number of carbon atoms. A "$C_{1-12}$ alkyl" refers to alkyl group having 1 to 12 carbon atoms. Examples of alkyl groups include, without limitation, methyl, ethyl, n-propyl, iso-propyl, n-butyl, sec-butyl, iso-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl and the like.

As used herein, the term "cycloalkyl" refers to saturated monocyclic and bicyclic hydrocarbon rings, generally having a specified number of carbon atoms that comprise the ring i.e. $C_{3-7}$ cycloalkyl refers to a cycloalkyl group having 3,4,5,6 and 7 carbon atoms as ring members. Examples of monocyclic groups include, without limitation, cyclopropyl, cyclobutyl, cyclopentyl, cyclohexyl, and the like. Examples of bicyclic cycloalkyl groups include without limitation, bicyclo[1.1.0]butyl, bicyclo[1.1.1]pentyl, bicyclo[2.1.0]pentyl, bicyclo[2.1.1]hexyl, bicyclo[2.2.0]hexyl, bicyclo[3.1.0]hexyl, bicyclo[2.2.1]heptyl, bicyclo[3.2.0]heptyl and the like.

As used herein, the term "aryl-$C_{1-6}$ alkyl" refers to an aryl group attached to the substrate through an alkyl group containing one to six carbon atoms. The term "aryl" refers to monovalent or divalent aromatic groups respectively including 5 and 6 membered monocyclic aromatic groups that contain zero to four heteroatom independently selected from nitrogen, oxygen and sulfur. Examples of monocyclic aryl groups include, without limitation, phenyl, pyrrolyl, pyranyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyradazinyl, pyrimidinyl, and the like. The aryl groups also include bicyclic groups, tricyclic groups etc including fused 5 and 6 membered rings described above. Examples of multicyclic aryl groups include, without limitation, naphthyl, biphenyl, anthracenyl, pyrenyl, carbazolyl, benzoxazolyl, benzodioxazolyl, benzothiazolyl, benzoimidazolyl, benzothiophenyl, quinolinyl, isoquinolinyl, indolyl, benzofuranyl, purinyl, indolizinyl and the like. The aryl groups may be attached to the substrate at any ring atom, unless such attachment would violate valence requirements. Aryl groups may include one or more non hydrogen substituents unless such substitution would violate valence requirements. Useful substituents include, without limitation alkyl, alkenyl, alkynyl, haloalkyl, alkoxy, halo, hydroxy, mercapto, nitro, amino, alkyl amino and the like.

The first aspect of the present invention deals with a process for the preparation of novel intermediate of general formula-28, which is useful for the synthesis of pregabalin. The process comprises of;
a) condensation of aldehyde compound of formula-15,

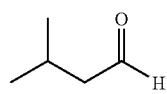

Formula-15 with an α-halo ester compound of formula-16,

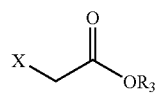

Fomula-16 wherein $R_3$ is a $C_{1-12}$ alkyl, $C_{3-7}$ cycloalkyl, or aryl-$C_{1-6}$ alkyl, and X is a halogen, in the presence of zinc metal and a suitable catalyst, in a suitable polar solvent provides (3-hydroxy ester compound of formula-17,

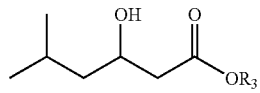

Formula-17 wherein $R_3$ is as defined above, b) hydrolysis of the (3-hydroxy ester compound of formula-17, with an alkali or alkaline metal base, in a protic solvent provides a β-hydroxy acid compound of formula-18,

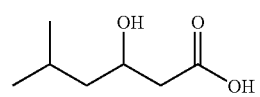

Formula-18 c) reacting the β-hydroxy acid compound of formula-18, with an halogenating agent in an aprotic solvent, followed by subsequent reaction with an secondary amine $NHR_1R_2$ of formula-19, provides a β-halo amide compound of formula-20,

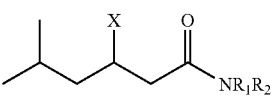

Fomula-20 wherein $R_1$ and $R_2$ are same or different and are each independently selected from either hydrogen, $C_{1-12}$ alkyl, $C_{3-7}$ cycloalkyl, aryl-$C_{1-6}$ alkyl, aryl or chiral auxiliaries (S/R) like 4-phenyl-2-oxazolidone, N-octyl glucamine, 1-phenyl ethyl amine and the like.

d) treating the β-halo amide compound of formula-20, with an cyanide source in an polar aprotic solvent, provides the novel intermediate the β-cyano amide, compound of formula-28,

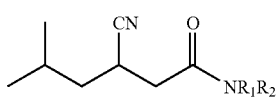

Formula-28 wherein $R_1$ and $R_2$ are as defined above.

Step (a) involves the condensation of aldehyde compound with the α-halo ester in presence of Zinc metal, using a catalyst preferably methane sulfonic acid in a polar solvent like tetrahydrofuran, dimethyl acetamide, dimethyl sulfoxide and the like preferably tetrahydrofuran. The halogen of the α-halo ester may be chlorine or bromine, preferably bromine.

Step (b) involves the hydrolysis of the (β-hydroxy ester derivative to the corresponding acid with a suitable base in a suitable solvent. Suitable inorganic bases that can be used in the reaction include but are not limited to hydroxides of alkali and alkaline earth metals such as lithium hydroxide, sodium hydroxide, potassium hydroxide and the like; carbonates of alkali metals such as sodium carbonate, potassium carbonate and the like and bicarbonates of alkali metals such as sodium bicarbonate, potassium bicarbonate and the like, preferably potassium hydroxide. Suitable solvents that can be used in the hydrolysis include but are not limited to alcoholic solvents such as methanol, ethanol, isopropanol preferably methanol and the like; water and their mixtures.

Step (c) involves the reaction of β-hydroxy acid compound with a halogenating agent to provide a β-halo acid chloride derivative which on subsequent reaction with a secondary amine ($NHR_1R_2$) provides a β-halo amide derivative. The halogen in β-position may be a chlorine or bromine. The suitable halogenating agent that can be used in the reaction but not limited to, are thionyl chloride ($SOCl_2$), phosphorus trichloride ($PCl_3$), phosphorus pentachloride ($PCl_5$), phosphorus oxychloride ($POCl_3$), phosphorus tribromide ($PBr_3$), phosphorus pentabromide ($PBr_5$) and the like, preferably thionyl chloride in an aprotic solvent. Solvents that can be used in the reaction include, without limitation, aromatic hydrocarbon solvents like toluene, xylene, or halogenated solvents such as dichloromethane, chloroform, ethylene dichloride and the like, preferably toluene.

In the subsequent step (d) the chloro group is substituted by cyano group by reacting it with a cyanide source such as but not limited to; hydrogen cyanide, acetone cyanohydrin, an alkali metal cyanide like sodium cyanide, potassium cyanide or an alkaline earth metal cyanide like magnesium cyanide and the like, preferably sodium cyanide, in a polar aprotic solvent dimethyl sulfoxide, dimethyl foramide, ethyl acetate, tetrahydrofuran, etc and their mixtures thereof preferably a mixture of dimethyl sulfoxide and ethyl acetate.

An alternate process for the preparation of novel intermediate of general formula-28, comprises of the following steps, a) Hydrolyzing the diester compound of formula-21,

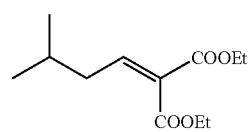

Formula-21 in presence of a suitable alkali metal or alkaline earth metal base in a suitable solvent gives the carboxylic acid compound of formula-22,

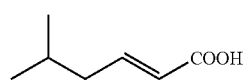

Formula-22 b) reacting the carboxylic acid compound of formula-22 with a suitable amine ($NHR_1R_2$), in presence of a suitable organic solvent gives an amide compound of general formula-23,

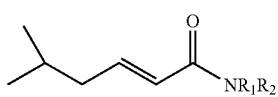

Formula-23 wherein $R_1$ and $R_2$ are same or different and are each independently selected from either hydrogen, $C_{1-12}$ alkyl, $C_{3-7}$ cycloalkyl, aryl-$C_{1-6}$ alkyl, aryl or chiral auxiliaries (S/R) like 4-phenyl-2-oxazolidone, N-octyl glucamine, 1-phenyl ethylamine and the like, c) reacting the amide compound of general formula-23 with a suitable cyanide source in presence of a phase transfer catalyst in a suitable solvent gives cyanide compound of general formula-28,

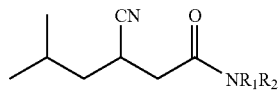

Formula-28 wherein $R_1$ and $R_2$ are as defined above.

In step a) the suitable alkali metal or alkaline earth metal base used for hydrolysis is selected from hydroxides like sodium hydroxide, potassium hydroxide, lithium hydroxide, cesium hydroxide, magnesium hydroxide, calcium hydroxide and the like; carbonates of alkali and/or alkaline earth metals such as sodium carbonate, potassium carbonate and the like and bicarbonates of alkali and/or alkaline earth metals such as sodium bicarbonate, potassium bicarbonate and the like, preferably potassium hydroxide in a suitable alcoholic solvent like methanol, ethanol, isopropanol, n-propanol, n-butanol, isobutanol, preferably methanol.

In the step b) the condensation of the amine with the carboxylic acid compound of formula-22 is carried out in the presence of thionyl chloride in a suitable aprotic solvent like cyclohexane, dichloromethane, trichloromethane, 1,2-dicholoroethane, toluene, xylene, tetrahydrofuran, 2-methyltetrahydrofuran, and the like; preferably toluene.

The cyanide source which is used in step c) is selected from the group consisting of but not limited to hydrogen cyanide, acetone cyanohydrin, an alkali metal cyanide like sodium cyanide, potassium cyanide or an alkaline earth metal cyanide like magnesium cyanide; trimethylsilyl cyanide and the like; preferably potassium cyanide.

The reaction is carried out in the presence/or absence of a phase transfer catalyst which is selected from the group consisting of but not limited to tetra butyl ammonium bromide, tetra propyl ammonium bromide, tributyl benzyl ammonium bromide, tetra octyl ammonium bromide, tetra butyl ammonium iodide, tetra butyl ammonium hydrogen sulfate, benzyl trimethyl ammonium chloride, benzyl triethyl ammonium chloride, tetra butyl ammonium acetate, tetra butyl ammonium iodide, ethyl triphenyl phosphonium bromide, more preferably tetra butyl ammonium bromide or alkali iodides like sodium iodide, potassium iodide and lithium iodide. The polar protic solvent used is selected from methanol, ethanol, n-propanol, isopropanol, n-butanol, and isobutanol; or water, or a mixture of water and alcohols; or it can be performed in presence of a polar aprotic solvent like dimethylsulfoxide or a mixture of dimethylsulfoxide and water or acetate.

The present aspect of the invention is represented in scheme-5.

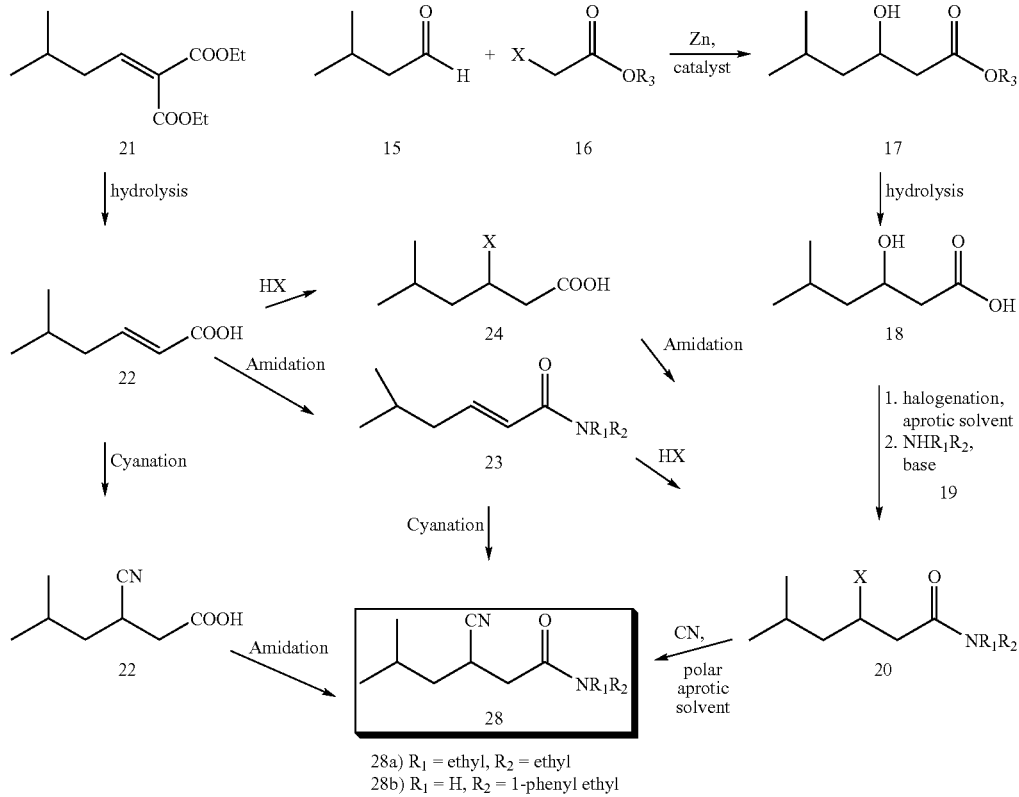

28a) $R_1$ = ethyl, $R_2$ = ethyl
28b) $R_1$ = H, $R_2$ = 1-phenyl ethyl

Wherein in $R_1$ and $R_2$ are same or different and are each independently selected from either hydrogen, $C_{1-12}$ alkyl, $C_{3-7}$ cycloalkyl, aryl-$C_{1-6}$ alkyl, aryl or chiral auxillaries (S/R) like 4-phenyl-2-oxazolidone, N-octyl glucamine, 1-phenyl ethylamine and the like; $R_3$ is a $C_{1-12}$ alkyl, $C_{3-7}$ cycloalkyl, or aryl-$C_{1-6}$ alkyl, and X is a halogen, The second aspect of the present invention relates to the preparation of novel intermediate of general formula-29, useful in the synthesis of pregabalin. The process for the synthesis of the novel intermediate comprises of a) Reaction of 3-isobutylglutaric acid anhydride compound of formula-3,

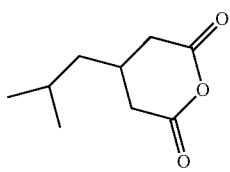

Formula-3 with a secondary amine $NHR_1R_2$ of general formula-19, in a suitable solvent, provides a compound of general formula-26,

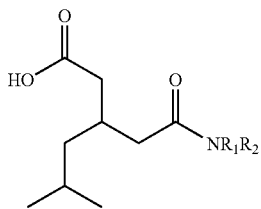

Formula-26 wherein $R_1$ and $R_2$ are same or different and are each independently selected from $C_{1-12}$ alkyl, $C_{3-7}$ cycloalkyl, aryl-$C_{1-6}$ alkyl, aryl or chiral auxiliaries (S/R) like 4-phenyl-2-oxazolidone, N-octyl glucamine, 1-phenyl ethylamine and the like.

b) reaction of compound of general formula-26, with thionyl chloride followed by ammonia provides the diamide compound of general formula-27,

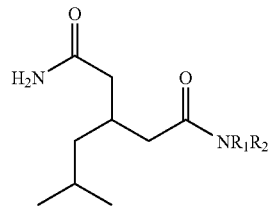

Formula-27 c) subjecting the compound of formula-27 to Hoffman's degradation provides the compound of general formula-29,

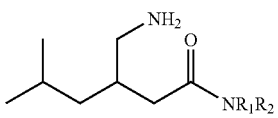

Formula-29

In the step a) of the above process the suitable solvent that can be used include, without limitation, aromatic hydrocarbon solvents like toluene, xylene, or halogenated solvents such as dichloromethane, chloroform, ethylene dichloride and the like, preferably dichloromethane.

In the step b) of the above process the suitable solvent that can be used include, without limitation, aromatic hydrocarbon solvents like toluene, xylene, or halogenated solvents such as dichloromethane, chloroform, ethylene dichloride and the like, preferably dichloromethane.

In the step c) of the above process the amide in subjected to Hoffmann's degradation using conventional methods known in prior art.

The second aspect of the present invention is represented in scheme-6.

Scheme-6

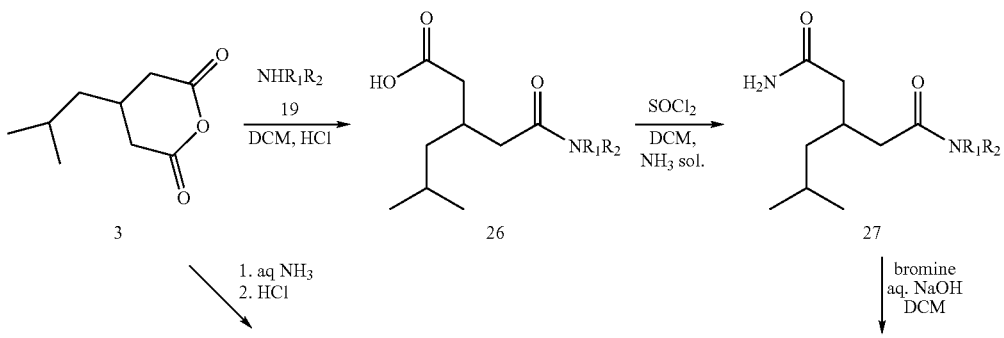

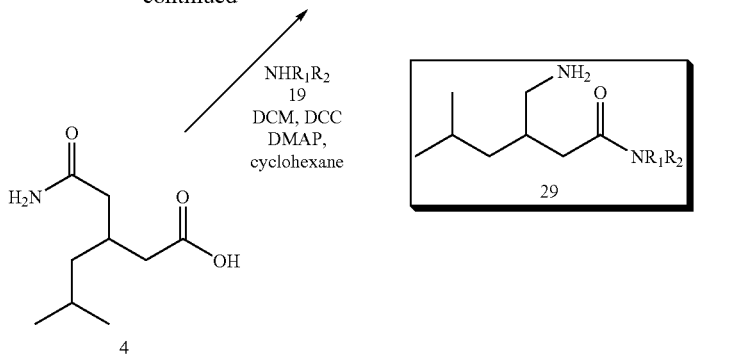

4

Wherein in $R_1$ and $R_2$ are same or different and are each independently selected from $C_{1-12}$ alkyl, $C_{3-7}$ cycloalkyl, aryl-$C_{1-6}$ alkyl, aryl or chiral auxillaries (S/R) like 4-phenyl-2-oxazolidone, N-octyl glucamine, 1-phenyl ethylamine and the like.

The third aspect of the present invention relates to the process for the preparation of (S)-pregabalin involving the novel intermediates compounds namely 3-cyano-5-methyl hexanamide compounds of general formula-28 and 3-(aminomethyl)-5-methyl hexanamide compounds of general formula-29. The process comprises of:

a) Reducing cyano group of the β-cyano amide, compound of formula-28,

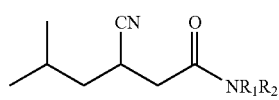

Formula-28 with a suitable reducing agent provides the amino amide derivative, compound of formula-29,

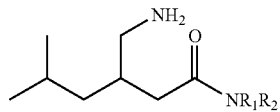

Formula-29 wherein in $R_1$ and $R_2$ are same or different and are each independently selected from either hydrogen, $C_{1-12}$ alkyl, $C_{3-7}$ cycloalkyl, aryl-$C_{1-6}$ alkyl, aryl or chiral auxiliaries (S/R) like 4-phenyl-2-oxazolidone, N-octyl glucamine, 1-phenyl ethylamine and the like.

b) reacting the amino derivative, compound of formula-29, with optically active organic acid provides a diastereomeric salt of formula-30,

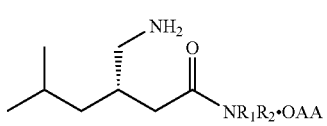

Formula-30 wherein $R_1$ and $R_2$ are as defined above, c) treating the diastereomeric salt of formula-30, with a base provides the compound of formula-31,

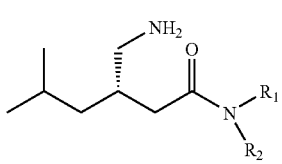

Formula-31 wherein $R_1$ and $R_2$ are as defined above, d) hydrolysis of the compound of formula-31, with a base in a suitable solvent provides (S)-pregabalin compound of formula-1,

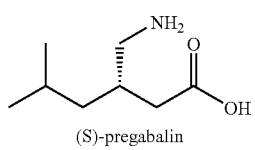

(S)-pregabalin e) purification of the (S)-pregabalin formed in the previous step, provides highly pure (S) pregabalin substantially free of impurities.

In Step a) the cyano moiety of the compound of formula-28 is reduced to give the amine compound of formula-29. The reduction can be performed using a number of catalysts in presence of hydrogen. These include, without limitation heterogeneous catalysts containing from about 0.1% to about 20% by weight of transition metals such as Ni, Pd, Pt, Rh, Re, Ru and Ir, including oxides and combination thereof, which are typically supported on various materials including $Al_2O_3$, C, $CaCO_3$, $SrCO_3$, $BaSO_4$, MgO, $SiO_2$, $TiO_2$, $ZrO_2$ and the like. Many of these metals including Pd may be doped with an amine, sulfide or a second metal such as Pb, Cu and Zn. Useful catalysts include raney nickel, palladium catalyst such as Pd/C, Pd/$SrCO_3$, Pd/$Al_2O_3$, Pd/MgO, Pd/$CaCO_3$, Pd/$BaSO_4$, PdO, Pd Black, $PdCl_2$ and the like. Other useful catalysts Rh/C, Ru/C, Re/C, $PtO_2$, Rh/C, $RuO_2$. The reaction is typically carried out in the presence of one or more polar solvents including without limitation water, alcohols, ethers, ester and acids such as, methanol, ethanol, isopropyl alcohol, tetrahydrofuran, ethyl acetate, acetic acid and the like. The preferred reducing agent in the present embodiment is Raney nickel in presence of hydrogen.

Step b) involves the separation of the recemic mixtures of compound of formula-29 by treating it with optically active organic acid to provide the diasteriomeric salt of formula-30. The chiral resolving agent is selected from optically active acid (OAA) like mandelic acid, camphor sulfonic acid and tartaric acid, most preferably tartaric acid. The reaction is performed in a suitable alcoholic solvent like methanol, ethanol, isopropanol, n-propanol, n-butanol, isobutanol; and water or their mixtures thereof.

Step c) involves the treatment of the diastereomeric salt of formula-30 with base which may include but not limited to alkali and alkali metal hydroxides, carbonates, hydrogen carbonates such as sodium hydroxide, potassium hydroxide, sodium carbonate, potassium carbonate, sodium hydrogen carbonate or potassium hydrogen carbonate and the like, preferably sodium hydroxide, in a suitable solvent like chloro hydrocarbon like dichloromethane, trichloromethane, 1,2-dichloroethane, preferably dichloromethane, to provide a free base of formula-31, which on subsequent (in-situ/or after isolation as a free base) hydrolysis provides (S)-Pregabalin.

The hydrolysis in step d) can be carried out with a suitable base in a suitable solvent. Suitable inorganic bases which can be used in the reaction include but are not limited to hydroxides of alkali and alkaline metals such as lithium hydroxide, sodium hydroxide, potassium hydroxide and the like; carbonates of alkali and alkaline metals such as sodium carbonate, potassium carbonate and the like and bicarbonates of alkali and alkaline metals such as sodium bicarbonate, potassium bicarbonate and the like, most preferably potassium hydroxide. Suitable solvents that can be used in the hydrolysis include but are not limited to; alcoholic solvents such as methanol, ethanol, isopropanol and the like: water: and their mixtures.

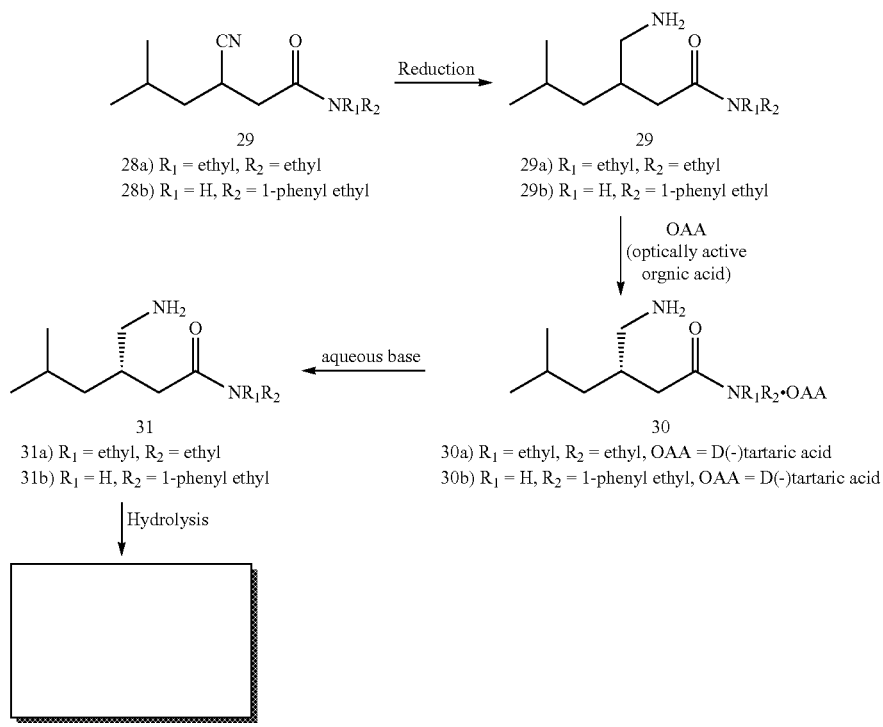

The fourth aspect of the present invention relates to a cost effective and economically useful method for the preparation of (S)-pregabalin. Though a number of methods are known in prior art for the synthesis of (S)-pregabalin they are burdened with drawbacks such as use of toxic chemicals or high costs of production etc.

The present invention has developed a cost effective process for the synthesis of (S)-pregabalin, by increasing the yields of the final product formed, and the recovery of the costly reagents used in the process and recycling them, which has reduced the cost of the production substantially.

A process for the production of (S)-pregabalin disclosed in U.S. Pat. No. 5,637,767 utilizes S-(+) mandelic acid for the resolution of the racemic mixture of pregabalin. The yield of pregabalin was found to be very low and the amount of S-(+) mandelic acid consumed was very high. The consumption of S-(+) mandelic acid is very high i.e. nearly at the ratio of 2 moles per one mole of (S)-pregabalin resolved. It is observed that only a partial amount of (S)-pregabalin is involved in the formation of the diastereomeric salt per mole of S-(+) mandelic acid added. To enrich the chiral purity, the diastereomeric salt it is treated with additional mandelic acid in the subsequent step. This leads to the addition of lager amounts of S-(+) mandelic acid, most of which remains unreacted in the reaction mixture, which is lost during workup.

To overcome the above drawbacks the present invention has devised a method to recover the S-(+) mandelic acid from the mother liquors (filtrate) and recycle it, so that it can again be used in the reaction. This resulted in the decrease in the overall amount of S-(+) mandelic acid consumed. The invention further involves the recovery of (S)-pregabalin from the mother liquors (filtrate) which led to the substantial increase in the final product. These two aspects have assisted in decreasing the cost of production to a large extent. The enantiomeric mixture of pregabalin (34) used for resolution in the present embodiment can be prepared by any of the methods depicted in scheme-8.

The process for the recovery of S (+) mandelic acid comprises of:
a) Separation of diastereomeric mandelate salt of (S)-pregabalin, from a solution obtained by the treatment of (R & S) mixture of pregabalin with S (+) mandelic acid in isopropanol and water mixture,
b) collecting the mother liquor from step a) and distilling off the solvent to obtain a residue,
c) dissolving the residue in water, and on subsequent acidification with concentrated hydrochloric acid to adjust the pH to 2 to 3,
d) cooling the reaction mixture,
e) separating the solid S (+) mandelic acid by filtration.

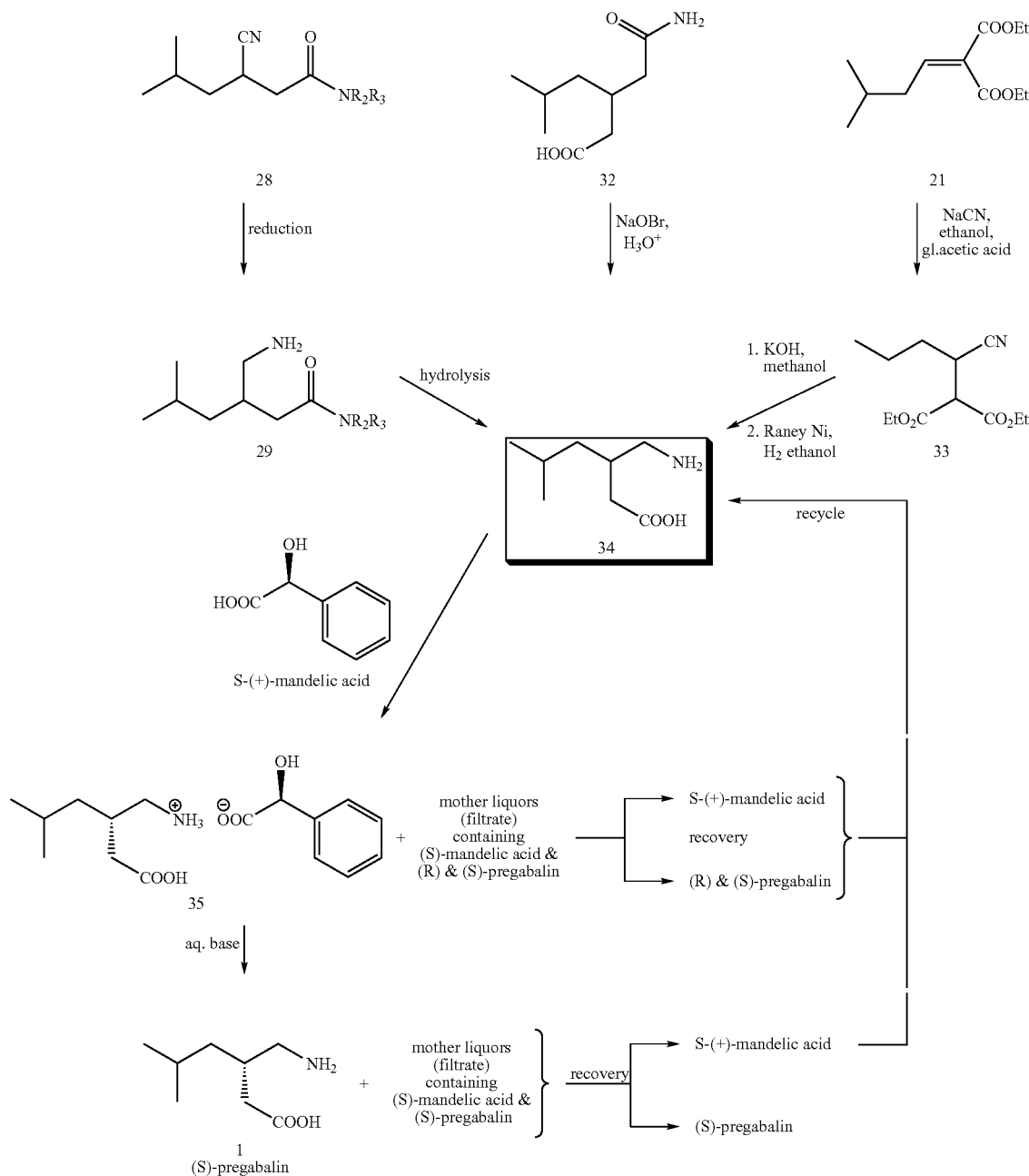

Scheme-8

The process for the recovery of pregabalin comprises of
  a) Separation of diastereomeric mandelate salt of (S)-pregabalin, from a solution obtained by the treatment of (R & S) mixture of pregabalin with S (+) mandelic acid in isopropanol and water mixture,
  b) collecting the mother liquor from step a) and distilling off the solvent to obtain a residue,
  c) dissolving the residue in water, and on subsequent acidification with concentrated hydrochloric acid to adjust the pH to 2 to 3, cooling the reaction mixture and separating the solid S (+) mandelic acid by filtration,
  d) collecting the mother liquors from step c) and treating it with a base to adjust the pH to 6-7,
  e) cooling the reaction mixture to precipitate the pregabalin,
  f) separating the solid pregabalin by filtration.

Analysis of Particle Size Distribution of Pregabalin:

A Malvern laser diffraction instrument was used to characterize the particle size distribution of pregabalin.

Instrument model: Malvern Mastersizer 2000
Technique used: Dry method
Instrument Parameters:
  i) Material RI: 1.500
  ii) Dispersant RI: 1.000
  iii) Analysis model: general purpose
  iv) Sensitivity: Normal The process described in the present invention was demonstrated in examples illustrated below. These examples are provided as illustration only and therefore should not be construed as limitation of the scope of the invention.

EXAMPLES

Example 1

Preparation of
3-cyano-N,N-diethyl-5-methylhexanamide

Step a): Preparation of tertiary butyl-3-hydroxy-5-methyl hexanoate

A solution of tetrahydrofuran (250 ml), Zinc dust (57 grams) and methane sulfonic acid (5 ml) was heated to reflux and stirred for 1 hour. Added isovalaraldehyde (50 grams) followed by tert-butyl bromoacetate (17 grams) to the reaction mixture. Stirred for twenty minutes. Added tert-butyl bromoacetate (157 grams) and stirred for 1 hour at reflux temperature. The reaction mixture was cooled to 25-35° C. and poured into solution of precooled concentrated hydrochloric acid. The reaction mixture was extracted with ethyl acetate. The organic layer washed with sodium bicarbonate solution, followed by water and dried over sodium sulfate. The solvent was distilled off under reduced pressure at a temperature below 50° C. to get the title compound as a residue.

Yield: 92 grams.

Step b): Preparation of 3-hydroxy-5-methyl hexanoic acid

To a solution of potassium hydroxide (11 grams) in methanol (50 ml), tertiary butyl-3-hydroxy-5-methyl hexanoate (40 grams dissolved in 40 ml methanol) was added very slowly with constant stirring at 20-30° C. The reaction mixture stirred for 4 hour at 20-30° C. Distilled off the solvent under reduced pressure at temperature below 45° C. Added water (90 ml) to the reaction mixture and washed the aqueous layer with dichloromethane. Discarded the organic layer and adjusted the pH aqueous layer to 2.0 using concentrated hydrochloric acid. Extracted the reaction mixture with dichloromethane. Distilled off the solvent under reduced pressure, at a temperature below 40° C. to yield the title compound as a residue.

Yield: 19 grams.

Step c): Preparation of 3-chloro-N,N-diethyl-5-methyl hexanamide

To a solution of 3-hydroxy-5-methyl hexanoic acid (3.5 grams) in toluene (18 ml), thionyl chloride (5.2 ml) was added and heated to 75° C. The reaction mixture was stirred at 75-80° C. for 2 hrs, and the solvent was distilled off under reduced pressure and temperature below 60° C. The reaction mixture was cooled to 0-5° C., diethyl amine was added and stirred at 0-5° C. for 30 min. Quenched the reaction mixture with water. The reaction mass was extracted with toluene. The solvent was distilled off under reduced pressure and temperature below 75° C. to obtain the title compound as a residue.

Yield: 3.6 grams.

Step d): Preparation of 3-cyano-N,N-diethyl-S-methylhexanamide

A suspension of 3-chloro-N,N-diethyl-5-methyl-hexanamide (1 gram), sodium cyanide (0.5 gram) in dimethylsulfoxide (10 ml) was heated to 75° C. and stirred at this temperature for 25 hrs. The reaction mixture was then cooled to 25-30° C. and quenched with water. The reaction mixture was extracted with ethyl acetate. The ethyl acetate layer was washed with water and distilled off under reduced pressure at a temperature below 60° C. to obtain the title compound as a residue.

Yield: 0.7 gram.

Example-2

Preparation of
3-cyano-N,N-diethyl-5-methylhexanamide
(Alternate Method)

Step a): Preparation of 5-methylhex-2-enoic Acid

To a solution of diethyl-2-(3-methylbutylidine) malonate (10 grams) in methanol (4 ml) cooled to 5° C., a solution of potassium hydroxide (6.75 grams in 11 ml of methanol) was added and stirred for 30 min at 7-9° C. The reaction mixture was heated to reflux temperature for 4.5 hours. The solvent was distilled off and quenched with water. The reaction mass was extracted with methylene chloride 20 ml. The pH of the reaction mixture was adjusted to 2 with hydrochloric acid. The resulting reaction mixture was extracted with dichloromethane. The solvent was distilled off completely under reduced pressure at 40° C. to obtain the title compound as a solid.

Yield: 4.2 grams.

Step b): Preparation of N,N-diethyl-5-methylhex-2-enamide

To a solution of 5-methylhex-2-enoic acid (formula-3) (20 grams) in dichloromethane (250 ml), 2 ml of dimethyl formamide was added. To this mixture thionyl chloride (24.1 grams) was added. The reaction mixture was stirred for 2.5 hours at 28-29° C. The reaction mixture was cooled to 0-5° C. and diethyl amine was added to the reaction mixture at 5-8° C. until the pH reached to 8.5. The reaction mixture was stirred for 1.5 hours at 0-5° C. The reaction mixture was quenched with water. Separated the aqueous and organic layers. The organic layer was washed with 5% sodium bicarbonate solution and was dried over anhydrous sodium sulphate. The solvent was distilled off completely under vacuum to provide the title compound as solid.

Yield: 17 grams

Step c): Preparation of 3-cyano-N,N-diethyl-5-methylhexanamide

Added 3.46 grams of compound N,N-diethyl-5-methylhex-2-enamide (formula-4-a) to a mixture of 0.863 gram of potassium cyanide and 3.5 grams of ethanol. Stirred the reaction mixture for 18 hours at 25-40° C. Added 4.45 ml of hexane to the reaction mixture. Added 0.875 gram of glacial acetic acid to the reaction mixture at 35° C. Quenched the reaction mixture with water. Separated the organic and aqueous phases. Extracted the aqueous phase with hexane. Washed the organic layer with water. Distilled the organic phase under reduced pressure to get the title compound as a residue Yield: 2.38 grams Example 3

Preparation of 3-aminomethyl-N,N-diethyl-5-methylhexanamide

Step a): Preparation of 3-(2-(diethyl amino)-2-oxoethyl)-methylhexanoic acid

To a solution of 3-isobutyl glutaric anhydride (5 grams) in dichloromethane (10 ml), added diethyl amine (4.3 grams) and stirred the reaction mixture for 12 hrs at 25° C. The reaction mixture was quenched with water (10 ml) and the pH of the reaction mixture adjusted to 1.0 using hydrochloric acid. The organic layer was separated and the aqueous layer was extracted with dichloromethane. The organic layers were combined and the solvent distilled off to provide the title compound as a residue.

Yield: 6.5 grams

Step b): Preparation of $N^1,N^1$-diethyl-3-isobutylpentane diamide

To a solution of 3-(2-(diethyl amino)-2-oxoethyl)-methylhexanoic acid (1 gram obtained in step-a) in dichloromethane (10 ml) and dimethylformamide (0.2 ml), thionyl chloride (0.5 gram) was added at a temperature below 5° C. Stirred the reaction mixture for 2 hrs. Ammonia solution (4 ml) was added to the reaction mixture at a temperature below 5° C. and stirred for 30 min. The reaction was quenched with water and the two layers were separated. The organic layer was washed with 2% hydrochloric acid followed by water. The solvent was distilled off to dryness to provide a title compound as a solid.

Yield: 0.6 gram

Step-c): Preparation of 3-aminomethyl-N,N-diethyl-5-methylhexanamide

To an aqueous solution of sodium hydroxide (2.8 grams in 3 ml of water), bromine (0.5 ml) was added and cooled to 5° C. $N^1,N^1$-diethyl-3-isobutylpentane diamide (0.6 gram, from the step-b) was added to the reaction mixture. Heated the reaction mixture to 80° C. and stirred for two hours. The reaction mixture was cooled to 30° C., quenched with water and the pH was adjusted to 2.0 using hydrochloric acid. Ethyl acetate was added to the reaction mixture, stirred and the two layers were separated. The pH of the aqueous layer was adjusted to 9 using sodium hydroxide and extracted with dichloromethane. Distilling off the solvent below 40° C. provided the title compound as a residue.

Yield: 0.5 gram

Example 4

Preparation of 3-aminomethyl-N,N-diethyl-5-methylhexanamide

To a solution of potassium hydroxide (19 grams) in methanol (114 ml), 3-cyano-N,N-diethyl-5-methyl hexanamide (9.5 grams) was added followed by ammonia solution (38 ml) and Raney nickel (19 grams). Hydrogen pressure of 4.0 kg/cm² was applied and the reaction mixture was stirred at 30° C. for 22 hours. The reaction mixture was filtered through a hyflow bed. The solvent was distilled off under reduced pressure at a temperature below 60° C. Water (200 ml) was added to the reaction mixture and pH adjusted to 2 with concentrated hydrochloric acid. The aqueous layer was extracted with dichloromethane. The pH of aqueous layer was adjusted to 8.0, with 50% sodium hydroxide. The aqueous layer was extracted with dichloromethane. The solvent was distilled off completely under atmospheric pressure to obtain the title compound as a residue.

Yield: 7.5 grams

Example 5

Preparation of 3-(aminomethyl)N,N-diethyl-5-methyl hexanamide D(−) tartarate salt 3-methyl amino N,N-diethyl-5-methyl hexanamide (10 grams) was suspended in water and added D (−) tartaric acid (7 grams). The reaction mixture was slowly heated to 40-45° C. and stirred for 30 min and filtered to remove the un-dissolved material. The filtrate was cooled to 20° C. and stirred at 15-20° C. for 1 hour. Filtered the solid obtained, washed with water and dried the material at 40-45° C. to obtain the title compound.

Yield: 6.1 grams.

Specific optical Rotation: $[\alpha]_D^{25}=-9.2°$ (c=1, water)

Example 6

Preparation of 3-(amino methyl) N,N-diethyl-5-methyl hexanamide L(+) tartarate salt 3-methyl amino N,N-diethyl-5-methyl hexanamide (10 gm) was suspended in water and added L(+) tartaric acid (7.0 gm). The reaction mixture was slowly heated to 40-45° C. and stirred for 30 min and filtered to remove the un-dissolved material. The filtrate was cooled to 20° C. and stirred at 15-20° C. for 1 hour. Filtered the solid obtained washed with water and dried the material at 40-45° C. to obtain the title compound Yield: 5.9 grams.

Specific optical Rotation: $[\alpha]_D^{25}=+9.2°$ (c=1, water)

Example 7

Preparation of (S)-Pregabalin

The tartarate salt of 3-aminomethyl N,N-diethyl-5-methyl hexanamide (10 grams) was dissolved in water (15 ml) and dichloromethane (25 ml) was added to it. The pH of reaction mixture was adjusted to 9-10 by addition of sodium hydroxide solution (3.0 gm NaOH in 3.0 ml of water) and stirred for 10-15 min at 20-25° C. The aqueous and organic layers were separated. The aqueous layer was extracted with dichloromethane. The aqueous layer was taken up for recovery of tartaric acid. The solvent was distilled off from combined organic layer to obtain a residue. Potassium hydroxide (5.0 grams) and water (5.0 ml) was added to the residue and heated to 115° C., the reaction was stirred at this temperature for 20 hours. The reaction mixture was cooled to 30° C. and the pH adjusted to 4.0 using concentrated hydrochloric acid. The reaction mixture was heated to 80° C. and stirred for 45 min and filtered. The filtrate was cooled to 5° C. and stirred for ninety minutes. The precipitated solid was filtered and washed with cool water. The solid was dried at 50-55° C. to yield (S)-Pregabalin.

Yield: 3.0 grams.

Example 8

Preparation of (S)-Pregabalin

The tartarate salt of 3-aminomethyl N,N-diethyl-5-methyl hexanamide (10 grams) was dissolved in water (15 ml) and dichloromethane (25 ml) was added to it. The pH of reaction mixture was adjusted to 9-10 by addition of sodium hydroxide solution (3.0 grams in 3.0 ml of water) and stirred for 10-15 min at 20-25° C. The aqueous and organic layer was separated. The aqueous layer was extracted with dichloromethane. The solvent was distilled off from combined organic layer to obtain a residue. Potassium hydroxide (5.0 gram), water (10 ml) and methanol (10 ml) was added to the obtained residue and heated it to 70-75° C., the reaction was stirred at this temperature for 18 hours. The reaction mixture was cooled to 30° C. and the pH adjusted to 4.0 using concentrated hydrochloric acid. The reaction mixture was heated to 80° C. and stirred for 45 min and filtered. The filtrate was cooled to 5° C. The solid formed was filtered and washed with cool water. The solid was dried at 50-55° C. to yield (S)-Pregabalin.

Yield: 3.6 grams.

Example 9

Purification of (S)-Pregabalin

A mixture of pregabalin (5 grams), isopropyl alcohol (100 ml) and water (25 ml) was heated to reflux temperature. The reaction mixture was stirred for 30 min at reflux temperature. The reaction mixture was filtered and the filtrate was cooled to 0-5° C. The reaction mixture was stirred for 2 hours at 0.5° C. The solid obtained was filtered, washed with mixture of isopropyl alcohol and water, and dried to get the pure pregabalin.

Yield: 3.8 grams.
Particle size distribution: D(0.1): 6.007 μm; D(0.5): 43.844 μm; D(0.9): 203.873 μm; D(1.00):508.24 μm.

Example 10

Recovery of R-isomer of 3-(aminomethyl) N,N-diethyl-5-methyl hexanamide and D(−) tartaric acid The mother liquors of example-5 and the aqueous layer of the example-7 and/or example-8, were combined and basified the reaction mixture with sodium hydroxide to adjust the pH to 8.5. The reaction mixture extracted with methylene chloride. Distilled off the solvent to get the R-isomer of 3-(methyl amino) N,N-diethyl-5-methyl hexanamide. The aqueous layer was treated with hydrochloric acid to adjust the pH to 2. Slowly cooled the reaction mixture to 0-5° C. and stirred for one hour. Filtered the precipitated solid and spin dried it to obtain D(−) tartaric acid, which was dried at 45°-50° C.

Yield: 3.0 grams (R-isomer).
Yield: 5.0 grams (D(−) tartaric acid)
Specific Optical Rotation: $[\alpha]_D^{20}=-12°$ (c=20, water)

Example 11

Recovery of Pregabalin from Filtered Mother Liquors

The solvent from the filtrate completely distilled off under reduced pressure. Isopropyl alcohol (10 ml) and water (5 ml) was added to the obtained mass. The contents were heated to reflux temperature and stirred for 30 minutes. The contents were cooled to 0-5° C. and stirred for 2 hrs. The obtained solid was filtered off and washed with a mixture of isopropyl alcohol and water. The solid was dried at 50-55° C. to obtain pure (S) Pregabalin.

Yield: 0.6 grams; Specific Optical Rotation: $[\alpha]_D^{25}=+11.0°$ (c=1, water)

Reference Example-A

Formation of Diastereomeric Salt of (S)-Pregabalin

To a solution of racemic pregabalin (1.2 kg) in isopropanol (24.0 lit) and water (0.72 lit), added S-(+) mandelic acid (1.6 kg) and the reaction mixture was heated to 50-55° C. with constant stirring. The reaction mixture was first cooled to 25-35° C. and then very slowly it was cooled to 0-5° C. Filtered the solid to get the diastereomeric salt.

Yield: 0.9 kg.

Reference Example-B

Preparation of (S)-Pregabalin

The mandalate salt of (S)-pregabalin (1.0 kg) was dissolved in tetrahydrofuran (20 lit) and water (0.6 lit). The mixture was heated to 60-65° C. and slowly cooled to 0-5° C. and stirred for one hour. Filtered the solid and washed with chilled tetrahydrofuran (0.1 lit). Spin dried the material to obtain the title compound.

Yield: 0.45 kg

Example 12

Recovery of Mandelic Acid

Distilled off the solvent from mother liquors of reference example-(A) and (B) separately under reduced pressure to obtain residue. The residues were combined and suspended in water (2.0 lit) and acidified the reaction mixture with hydrochloric acid to adjust the pH to 2. The mixture was heated to reflux and stirred for 4 hours. Slowly cooled the reaction mixture to 0-5° C. and stirred for one hour. Filtered the precipitated solid and spin dried it to obtain mandelic acid, which was dried at 45°-50° C.

Yield: 1.1 kg.
Specific Optical Rotation: $[\alpha]_D^{25}=+152°$ (c=2.8, water)

Example 13

Recovery of Pregabalin

The mother liquors from the example-12 was taken and neutralized with sodium hydroxide (20%) to adjust the pH to 6.7. The reaction mixture cooled to 0-5° C. The reaction mixture was stirred for 30 minutes at 0-5° C. The precipitated solid was filtered off and washed with chilled isopropyl alcohol to get pregabalin.

Yield: 0.65 kg.

Example-14

Resolution of Pregabalin using Recovered S (+)-Mandelic Acid

To a solution of racemic pregabalin (1.2 kg) in isopropanol (24 lit) and water (0.7 lit), added recovered S-(+) mandelic acid (1.2 kg) and the reaction mixture was heated to 50-55° C. with constant stirring. The reaction mixture was first cooled to 25-35° C. and then very slowly it was cooled to 0-5° C. The reaction mixture was filtered to isolate the diastereomeric salt formed.

Yield: 0.79 kg.

We claim:

1. A compound represented by the following structural formula:

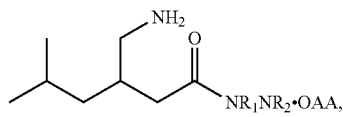

or an enantiomer thereof, wherein:
$R_1$ and $R_2$ are each ethyl, and
OAA is D-(−)-tartaric acid or L-(+)-tartaric acid.

2. A process for the preparation of a compound of Formula-30,

Formula-30

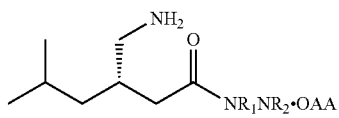

wherein $R_1$ and $R_2$ are each independently hydrogen, unsubstituted $C_{1-12}$ alkyl, $C_{3-7}$ cycloalkyl, aryl $C_{1-6}$ alkyl, or aryl, or $R_1$ and $R_2$, taken together with the nitrogen to which they are bound, form a chiral auxiliary (S/R) selected from 4-phenyl-2-oxazolidinone, N-octylglucamine and 1-phenylethylamine; and OAA is D-(−)-tartaric acid, the process comprising:

a) reacting a compound of Formula-3,

Formula-3

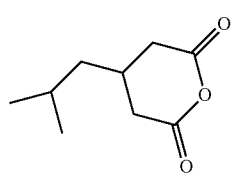

with a secondary amine $NHR_1R_2$, wherein $R_1$ and $R_2$ are as defined above, in a solvent to produce a compound of Formula-26, Formula-26

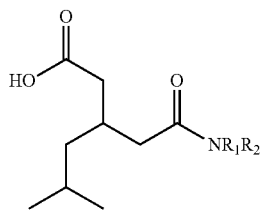

wherein $R_1$ and $R_2$ are as defined above;

b) reacting the compound of Formula-26 with thionyl chloride followed by ammonia to produce the diamide compound of Formula-27, Formula-27

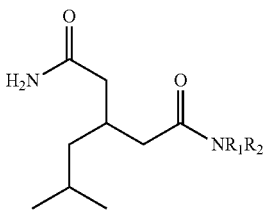

wherein $R_1$ and $R_2$ are as defined above;

c) subjecting the compound of Formula-27 to Hoffman's degradation to produce a compound of Formula-29, Formula-29

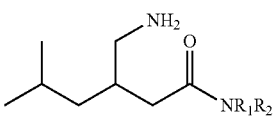

wherein $R_1$ and $R_2$ are as defined above; and d) reacting the compound of Formula-29 with D-(−)-tartaric acid in a solvent to produce the compound of Formula-30.

3. A process for the preparation of a compound of Formula-1, comprising:

a) reducing cyano group of a β-cyano amide compound of Formula-28,

Formula-28

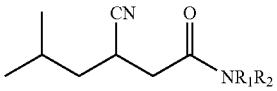

with a reducing agent in a solvent to produce the amino amide compound of Formula-29, Formula-29

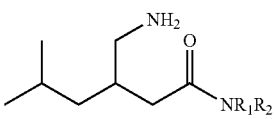

wherein $R_1$ and $R_2$ are each independently hydrogen, unsubstituted $C_{1-12}$ alkyl, $C_{3-7}$ cycloalkyl, aryl-$C_{1-6}$ alkyl, or aryl, or R₁ and R₂, taken together with the nitrogen to which they are bound, form a chiral auxiliary (S/R) selected from 4-phenyl-2-oxazolidinone, N-octylglucamine and 1-phenylethylamine b) reacting the compound of Formula-29 with D-(−)-tartaric acid in a solvent to produce diastereomeric salt of Formula-30,

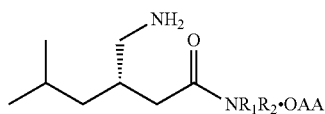

Formula-30 wherein R₁ and R₂ are as defined above and OAA is D-(−)-tartaric acid;

c) treating the diastereomeric salt of Formula-30 with a base to produce the compound of Formula-31,

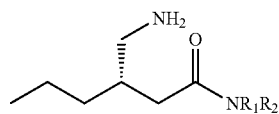

Formula-31 wherein R₁ and R₂ are as defined above;

d) hydrolyzing the compound of Formula-31 with a base in a solvent to produce a compound of Formula-1,

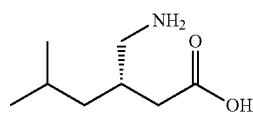

Formula-1 and;

e) removing impurities from the compound of Formula-1 formed in step d) to produce the compound of Formula-1 substantially free of impurities.

4. The process of claim 3, wherein the reduction of the cyano group in step a) is performed using hydrogen and the reducing agent is Raney nickel, a transition metal, an oxide thereof or a combination thereof.

5. The process of claim 4, wherein the reducing agent is Raney nickel.

6. The process of claim 3, wherein the solvent used in step a) is an alcohol, ether, ester, acid or water.

7. The process of claim 3, wherein the solvent used in step b) is methanol, ethanol, isopropanol, n-propanol, n-butanol, isobutanol, water or a mixture of water and alcohol.

8. A process for the preparation of a diastereomeric tartrate salt of the S-isomer of 3-methylamino-N,N-diethyl-5-methylhexanamide and for the recovery of the R-isomer of 3-methylamino-N,N-diethyl-5-methylhexanamide, comprising:

a) treating an (R and S) mixture of 3-methylamino-N,N-diethyl-5-methylhexanamide with D (−) tartaric acid in water, thereby forming the diastereomeric tartrate salt of the S-isomer of 3-methylamino-N,N-diethyl-5-methylhexanamide and a mother liquor, and separating the diastereomeric tartrate salt from the mother liquor; and b) basifying the mother liquor from step a) and extracting the R-isomer of 3-methylamino-N,N-diethyl-5-methylhexanamide with a solvent, thereby recovering the R-isomer of 3-methylamino-N,N-diethyl-5-methylhexanamide.

9. A process for the preparation of a diastereomeric tartrate salt of 3-methylamino-N,N-diethyl-5-methylhexanamide and for recovery of D (−) tartaric acid, comprising:

a) treating an (R and S) mixture of 3-methylamino-N,N-diethyl-5-methylhexanamide with D (−) tartaric acid in water, thereby forming the diastereomeric tartrate salt of the S-isomer of 3-methylamino-N,N-diethyl-5-methylhexanamide and a mother liquor, and separating the diastereomeric tartrate salt from the mother liquor;

b) basifying the mother liquor from step a) and extracting the R-isomer of 3-methylamino-N,N-diethyl-5-methylhexanamide with a solvent;

c) acidifying the mother liquor from step b) with concentrated hydrochloric acid to adjust the pH to 2 to 3;

d) cooling the mother liquor from step c), thereby forming solid D (−) tartaric acid; and e) separating the solid D (−) tartaric acid by filtration, thereby recovering D (−)tartaric acid.

10. The process of claim 3, wherein the substantially pure compound of Formula-1 produced in step e) has a mean particle size in the range of 50-90 μm and D (v. 0.9) in the range of 170-230 μm.

11. The process of claim 4, wherein the transition metal is Ni, Pd, Pt, Rh, Re, Ru, Ir, or a combination thereof.

12. The compound of claim 1, or an enantiomer thereof, wherein OAA is L-(+)-tartaric acid.

13. A compound represented by the following structural formula:

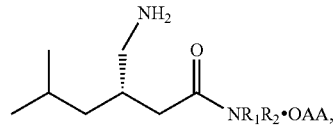

wherein R₁ and R₂ are each independently hydrogen, unsubstituted C₁₋₁₂ alkyl, C₃₋₇ cycloalkyl, aryl C₁₋₆ alkyl, or aryl, or R₁ and R₂, taken together with the nitrogen to which they are bound, form a chiral auxiliary (S/R) selected from 4-phenyl-2-oxazolidinone, N-octylglucamine and 1-phenylethylamine; and OAA is D-(−)-tartaric acid or L-(+)-tartaric acid.

14. The compound of claim 13, represented by the following structural formula:

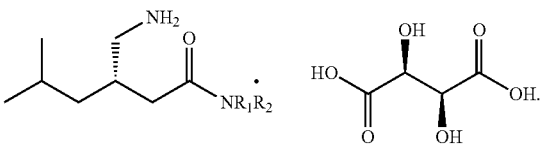

15. The process of claim 2, wherein R₁ and R₂ are each ethyl.

16. The process of claim 3, wherein R₁ and R₂ are each ethyl.

17. A process for the preparation of a compound of Formula-1, comprising:

a) reacting a compound of Formula-29,

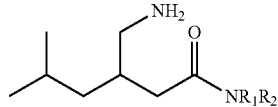

Formula-29 with D-(−)-tartaric acid in a solvent to produce a diastereomeric salt of Formula-30,

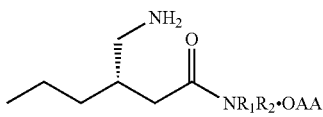

Formula-30 wherein $R_1$ and $R_2$ are each independently hydrogen, unsubstituted $C_{1-12}$ alkyl, $C_{3-7}$ cycloalkyl, aryl-$C_{1-6}$ alkyl, or aryl, or $R_1$ and $R_2$, taken together with the nitrogen to which they are bound, form a chiral auxiliary (S/R) selected from 4-phenyl-2-oxazolidinone, N-octylglucamine and 1-phenylethylamine; and OAA is D-(−)-tartaric acid b) treating the diastereomeric salt of Formula-30 with a base to produce the compound of Formula-31,

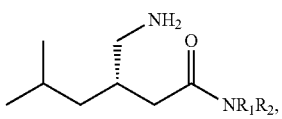

Formula-31 wherein $R_1$ and $R_2$ are as defined above;

c) hydrolyzing the compound of Formula-31 with a base in a solvent to produce a compound of Formula-1,

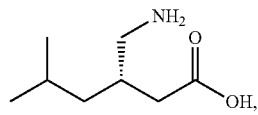

Formula-1 and;

d) removing impurities from the compound of Formula-1 to produce the compound of Formula-1 substantially free of impurities.

18. The compound of claim 17, wherein $R_1$ and $R_2$ are each ethyl.

19. The compound of claim 14, wherein $R_1$ and $R_2$ are each ethyl.

* * * * *

UNITED STATES PATENT AND TRADEMARK OFFICE
CERTIFICATE OF CORRECTION

| | | |
|---|---|---|
| PATENT NO. | : 8,168,828 B2 | Page 1 of 1 |
| APPLICATION NO. | : 12/666133 | |
| DATED | : May 1, 2012 | |
| INVENTOR(S) | : Manne Satyanarayana Reddy et al. | |

It is certified that error appears in the above-identified patent and that said Letters Patent is hereby corrected as shown below:

Claim 3, column 29, line 25, delete the chemical compound and insert:

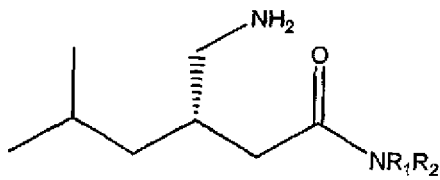

Formula-31

--    --

Claim 17, column 31, line 20, delete the chemical compound and insert:

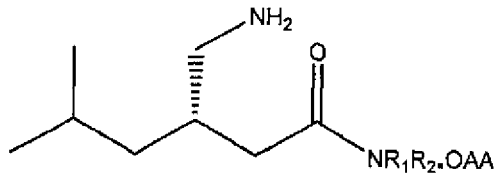

Formula-30

--    --

Signed and Sealed this
Twenty-sixth Day of June, 2012

David J. Kappos
*Director of the United States Patent and Trademark Office*